US00PP10385P

United States Patent [19]

Zaiger et al.

[11] Patent Number: Plant 10,385

[45] Date of Patent: May 12, 1998

[54] PLUM TREE "JOANNA RED"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesta, Calif. 95358

[21] Appl. No.: 771,862

[22] Filed: Dec. 23, 1996

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of plum tree (*Prunus salicina*) with the following features that are desirable in a new variety:

1. Vigorous, upright growth.
2. Heavy and regular production of medium to large size fruit.
3. Fruit with an attractive red skin color.
4. Relatively uniform ripening of fruit throughout the tree.
5. Fruit with good firmness, handling and shipping qualities.
6. Fruit with the ability to remain firm on the tree 6 to 7 days after shipping ripe.
7. The fruit having a good balance between acid and sugar with good flavor and eating quality.

1 Drawing Sheet

ORIGIN OF THE VARIETY

The present new variety of plum tree was originated by us in our experimental orchard located near Modesto, Calif., from a cross between the selected seedling with field identification number 46G731 and a plum of unknown parentage. The maternal parent (46G731) originated from a cross between Laroda Plum (non-patented) and Queen Ann Plum (non-patented). A large number of these first generation seedlings were grown by us and maintained under close observation, during which time one such seedling which is of the present variety, exhibited the distinct and desirable characteristics described above and was selected for asexual reproduction and commercialization.

ASEXUAL REPRODUCTION OF THE VARIETY

Asexual reproduction of the new and distinct variety of plum tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The present new and distinct variety of plum tree is of large size, vigorous, upright growth and a regular and productive bearer of medium to large, yellow flesh, freestone fruit with good flavor and eating quality. The fruit is further characterized by having firm flesh with good handling and shipping quality, relatively uniform ripening throughout the tree and the ability to hold firm on the tree 6 to 7 days after shipping ripe. In comparison to Casselman Plum (non-patented), the new variety ripens approximately 5 days earlier, with heavier production of larger size fruit and a greater degree of attractive red skin color.

PHOTOGRAPH OF THE VARIETY

The accompanying color photographic illustration shows typical specimens of the foliage and fruit of the present new plum variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of plum tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Productivity.*—Productive.
- *Bearer.*—Regular.
- *Density.*—Medium dense.

Trunk:
- *Size.*—Medium to large.
- *Texture.*—Medium shaggy.
- *Color.*—Grayish brown to soot brown (5-E-3) to (5-F-5).

Branches:
- *Size.*—Medium.
- *Texture.*—Smooth to medium rough.
- *Lenticels.*—Medium number. Small size.
- *Color.*—Brown to oak brown (5-D-4) to (5-D-6). Varies with age of growth.

Leaves:
- *Size.*—Large. Average length 3⅞". Average width 1⅝".
- *Form.*—Oblanceolate, pointed.
- *Margin.*—Crenate.
- *Thickness.*—Medium.
- *Surface.*—Smooth.
- *Petiole.*—Medium length. Medium thickness.
- *Glands.*—Number varies from 1 to 4. Average number 2. Globose. Primarily positioned on upper portion of the petiole and base of leaf blade.
- *Color.*—Upper surface — green to dark green (28-F-4) to (28-F-7). Lower surface — dull green to green (28-E-3) to (28-E-6).

Flower buds:
*Size.*—Medium.
*Length.*—Medium.
*Form.*—Plump.
Flowers:
*Size.*—Medium.
*Pollen.*—Present.
*Blooming period.*—Date of first bloom: Mar. 1, 1996. Date of full bloom: Mar. 6, 1996. Varies slightly with climatic conditions.
*Color.*—White.
Fruit:
*Maturity when described.*—Firm ripe.
*Date of first picking.*—Aug. 1, 1996.
*Date of last picking.*—Aug. 5, 1996. Varies slightly with climatic conditions.
*Size.*—Medium to large. Comparatively uniform. Average diameter axially 2¼". Average transversely in suture plane 2⅜".
*Form.*—Nearly globose, slightly flattened at stem end.
*Suture.*—Shallow, extends from base to apex.
*Ventral surface.*—Nearly rounded.
*Apex.*—Usually rounded, varies from slight tip to rounded.
*Base.*—Retuse.
*Cavity.*—Slightly elongated in suture plane. Average breadth ½". Average depth ⅜".
*Stem.*—Average length ½". Average thickness 1/16".
Flesh:
*Ripens.*—Evenly to slightly earlier at apex.
*Texture.*—Firm.
*Fibers.*—Small, tender.
*Aroma.*—Very slight.
*Eating quality.*—Good.
*Flavor.*—Good. Sweet, good balance between acid and sugar.
*Color.*—Pale yellow to light yellow (4-A-3) to (4-A-5). Pit cavity — grayish yellow to brownish yellow (5-B-3) to (5-B-5).
Skin:
*Thickness.*—Medium.
*Texture.*—Medium, tenacious to flesh.
*Bloom.*—Moderate.
*Down.*—Wanting.
*Tendency to crack.*—None.
*Color.*—Ground color light yellow to yellow (4-A-5) to (4-A-7). Nearly overspread with garnet red to brownish red (10-E-5) to (10-E-8). Small areas of ground color creating a speckling of randomly spaced dots.
Stone:
*Type.*—Freestone when fully mature.
*Size.*—Medium. Average length 1". Average width ¾". Average thickness ½".
*Form.*—Ovoid.
*Base.*—Varies from straight to rounded.
*Apex.*—Acuminate.
*Surface.*—Slightly pitted throughout. Shallow furrows near stem end extending toward apex, one long furrow on each side of suture.
*Sides.*—Mostly equal, varies from equal to unequal.
*Tendency to split.*—None.
*Color.*—Light brown to brown (5-C-5) to (5-D-5).
Use: Dessert. Market, local and long distance.
Keeping quality: Good.
Shipping quality: Good.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous, upright growth and being a regular and productive bearer of medium to large, yellow flesh, freestone fruit, having a good balance between acid and sugar to produce good flavor and eating quality; the fruit is further characterized by its firmness which facilitates its good handling and shipping qualities, the ability to remain firm on the tree 6 to 7 days after shipping ripe and in comparison to Casselman Plum (non-patented), the new variety has heavier production of larger size fruit with a greater degree of attractive red skin color and matures approximately 5 days earlier.

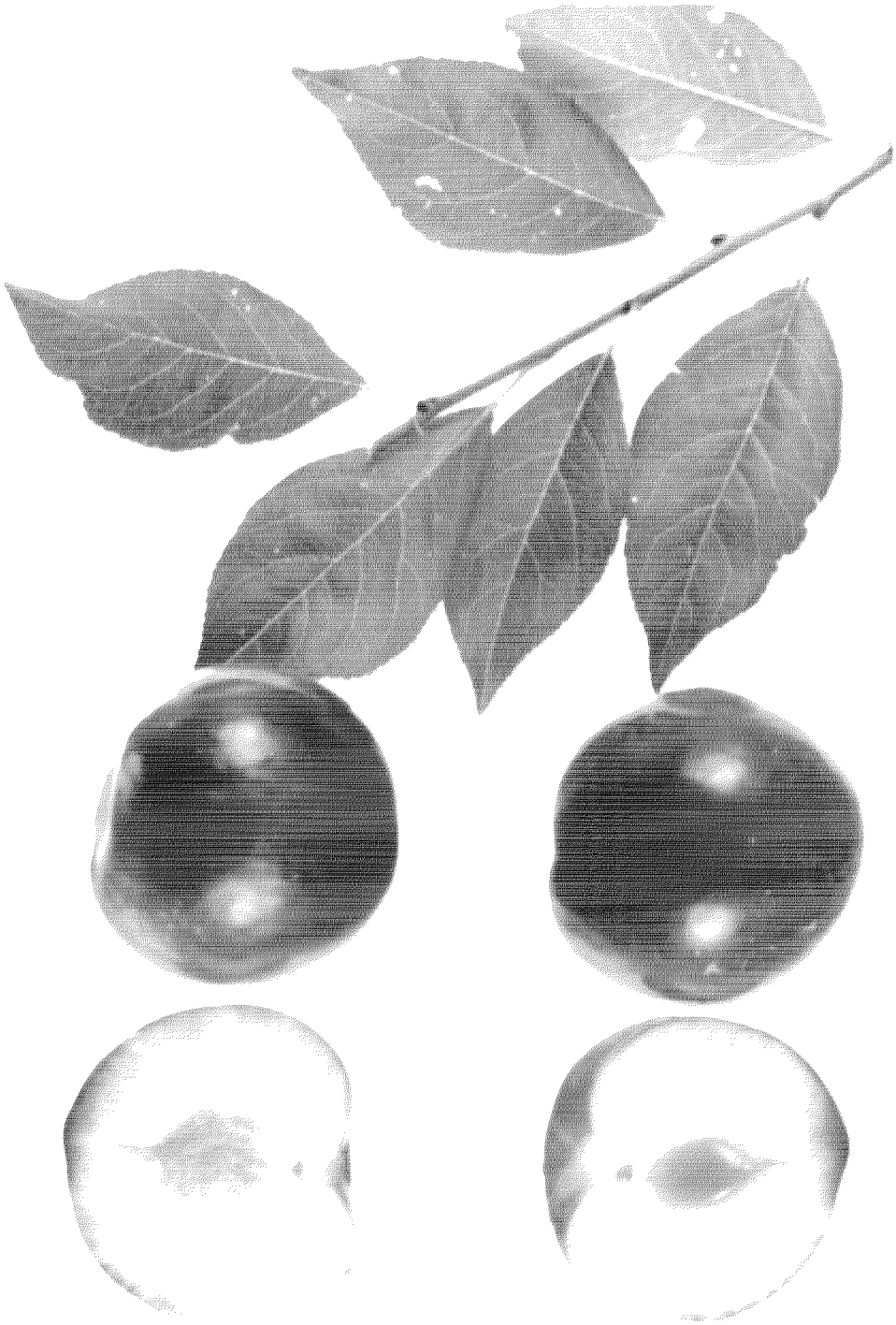

* * * * *